United States Patent [19]

Barkhoudarian

[11] Patent Number: 5,001,346
[45] Date of Patent: Mar. 19, 1991

[54] LEAK DETECTION SYSTEM WITH BACKGROUND COMPENSATION

[75] Inventor: Sarkis Barkhoudarian, Canoga Park, Calif.

[73] Assignee: Rockwell International Corporation, El Segundo, Calif.

[21] Appl. No.: 484,943

[22] Filed: Feb. 26, 1990

[51] Int. Cl.⁵ ............................................. G01N 21/35
[52] U.S. Cl. .................................. 250/330; 250/338.5; 250/339
[58] Field of Search ...................... 250/330, 338.5, 339

[56] References Cited

U.S. PATENT DOCUMENTS

| | | | |
|---|---|---|---|
| 3,857,052 | 12/1974 | Beller | 340/149 R |
| 3,982,425 | 9/1976 | McLain | 73/67.83 |
| 4,060,716 | 12/1977 | Pekrul et al. | 364/576 |
| 4,170,455 | 10/1979 | Henrie | 23/232 |
| 4,429,329 | 1/1984 | Clemens et al. | 358/100 |
| 4,432,931 | 2/1984 | Lockett | 376/248 |
| 4,462,082 | 6/1984 | Thiele et al. | 364/571 |
| 4,543,481 | 9/1985 | Zwick | 250/338.5 |
| 4,567,769 | 2/1986 | Barkhoudarian | 73/643 |
| 4,612,797 | 9/1986 | Barkhoudarian | 73/40.5 |
| 4,767,911 | 8/1988 | Maram et al. | 219/130.01 |
| 4,772,789 | 9/1988 | Maram et al. | 250/330 |
| 4,795,253 | 1/1989 | Sandridge et al. | 250/338.5 |
| 4,841,149 | 6/1989 | Martin et al. | 250/330 |

FOREIGN PATENT DOCUMENTS 0143242  8/1983  Japan ................ 250/338.5

OTHER PUBLICATIONS

"Gas Filter Correlation Instrument for the Remote Sensing of Gas Leaks", Lee et al. -Am. Inst. of Physics-Sep. '85.

Primary Examiner—Janice A. Howell
Assistant Examiner—Drew A. Dunn
Attorney, Agent, or Firm—H. Fredrick Hamann; Harry B. Field; Steven E. Kahm

[57] ABSTRACT

An improved leak detection system (10) of the differential absorption type is provided for identifying gas leaks in a test object (12), wherein the improved system (10) provides enhanced resolution and accuracy by compensating for the effects of background gases and the like along the image path. The system utilizes a video camera (18) to generate images of the test object (12) which has been pressurized with a selected gas (14) having strong absorption properties with respect to an illuminating light source (16) of a selected wavelength. Since the absorption bandwidth of the test gas (14) varies with temperature, the gas is preconditioned as by heating such that the temperature of gas leaking to the exterior of the test object (12) will vary with proximity to the test object. The camera (18) observes the pressurized test object in sequence through filters (30, 32) of narrow and broad bandwidth to generate a pair of images which can be electronically compared to isolate upon the test gas (14) located substantially at a specific leakage site or sites on the test object.

13 Claims, 2 Drawing Sheets

COMPOSITE IMAGE

LEAK IMAGE

LEAK DETECTION SYSTEM WITH BACKGROUND COMPENSATION

BACKGROUND OF THE INVENTION

This invention relates generally to systems and methods for detecting and quantifying leaks in test objects through the use of differential absorption techniques. More particularly, this invention relates to an improved leak detection system designed to compensate for or disregard the masking effects of background gas, moisture, etc., which can otherwise reduce system sensitivity and resolution.

Leak detection systems of the so-called differential absorption type are known in the art, for example, by reference to U.S. Pat. 4,772,789. In such systems, a selected test object such as a rocket engine or components thereof is internally charged or pressurized with a test gas chosen for its capacity to absorb light of a particular wavelength. The pressurized test object is then illuminated with a light source having a wavelength selected to correspond with the absorptive properties of the test gas, and a video camera is used to produce images of the test object. Any test gas leaking to the exterior of the test object will absorb light such that the camera image represents a composite of the test object and leaking gas, if present. Such composite image can be analyzed particularly by computer in comparison with a counterpart image generated with illumination at a nonabsorbing wavelength to identify and quantify gas leakage.

While differential absorption systems beneficially provide remote and noninvasive leak detection analysis with respect to test objects of virtually any size and shape, the read-out from such systems is sometimes masked by small background quantities of the test gas or other contaminants present within the camera image path. More specifically, in a leak test facility, residual quantities of the test gas are sometimes present in the foreground and/or background with respect to an illuminated test object, wherein such gas will absorb some of the illuminating radiation and thereby falsely contribute to system read-out. As a result, precise determination of the occurrence and location of small leaks may be difficult or impossible. Alternately, when a test object is monitored for leakage over a prolonged time period, test gas may accumulate about the test object and within the image path to obscure determination of actual leakage location or magnitude. Similarly, atmospheric contaminants such as particulate and/or water droplets disposed along the image path can absorb light and thereby reduce system sensitivity.

The present invention is therefore directed toward improvements in leakage detection systems of the differential absorption type, wherein the system compensates for light absorption attributable to background factors and thereby provides improved sensitivity with respect to actual test gas leakage from a test object.

SUMMARY OF THE INVENTION

In accordance with the invention, an improved system and related method are provided for leak detection analysis of a selected test object by means of differential absorption. The improved leak detection system is designed to compensate for light absorption attributable to background factors such as residual light absorbing gas and/or air-borne contaminants in the vicinity of the monitored test object. Such background compensation permits the present system to provide an accurate and highly sensitive indication of actual test object leakage.

The leak detection system employs a selected test gas having relatively strong absorptive properties with respect to light generally corresponding with a selected wavelength. The test gas is utilized to pressurize the selected test object, such as a rocket engine component, industrial process fluid piping or vessel, etc. The pressurized test object is then illuminated with a light source generally conforming to the selected wavelength corresponding with the absorptive properties of the test gas, and a video camera is used to generate images of the illuminated test object. To this point, the leak detection system corresponds with U.S. Pat. No. 4,772,789, which is incorporated by reference herein.

The present invention recognizes that the spectral absorption bandwidth of the test gas is functionally related to temperature, with the absorption bandwidth increasing in response to increasing temperature. Accordingly, the test gas used to pressurize the test object is temperature conditioned relative to the surrounding ambient temperature level, such as by preheating, whereby leaking test gas disposed immediately adjacent to the test object and corresponding directly with actual and on-going gas leakage will have a relatively higher temperature in comparison with background test gas disposed distant from the test object.

The video camera is operated in conjunction with a pair of bandwidth filters to provide a respective pair of images which can be analyzed in a manner compensating for absorption attributable to background gas. In particular, the test object and surrounding test gas are sequentially imaged through a relatively narrow bandwidth filter and a relatively broad bandwidth filter. The narrow band image represents absorption attributable to cooler or background gas, whereas the broad band image represents the combined absorption due to the background factors and the hotter test gas in close proximity with the test object. By comparing the two images preferably in accordance with the electronic image processor techniques described in U.S. Pat. No. 4,772,789, the effects of the background gas can be identified and disregarded to provide a final image read-out as a precision indication of heated test gas in close proximity to the test object.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
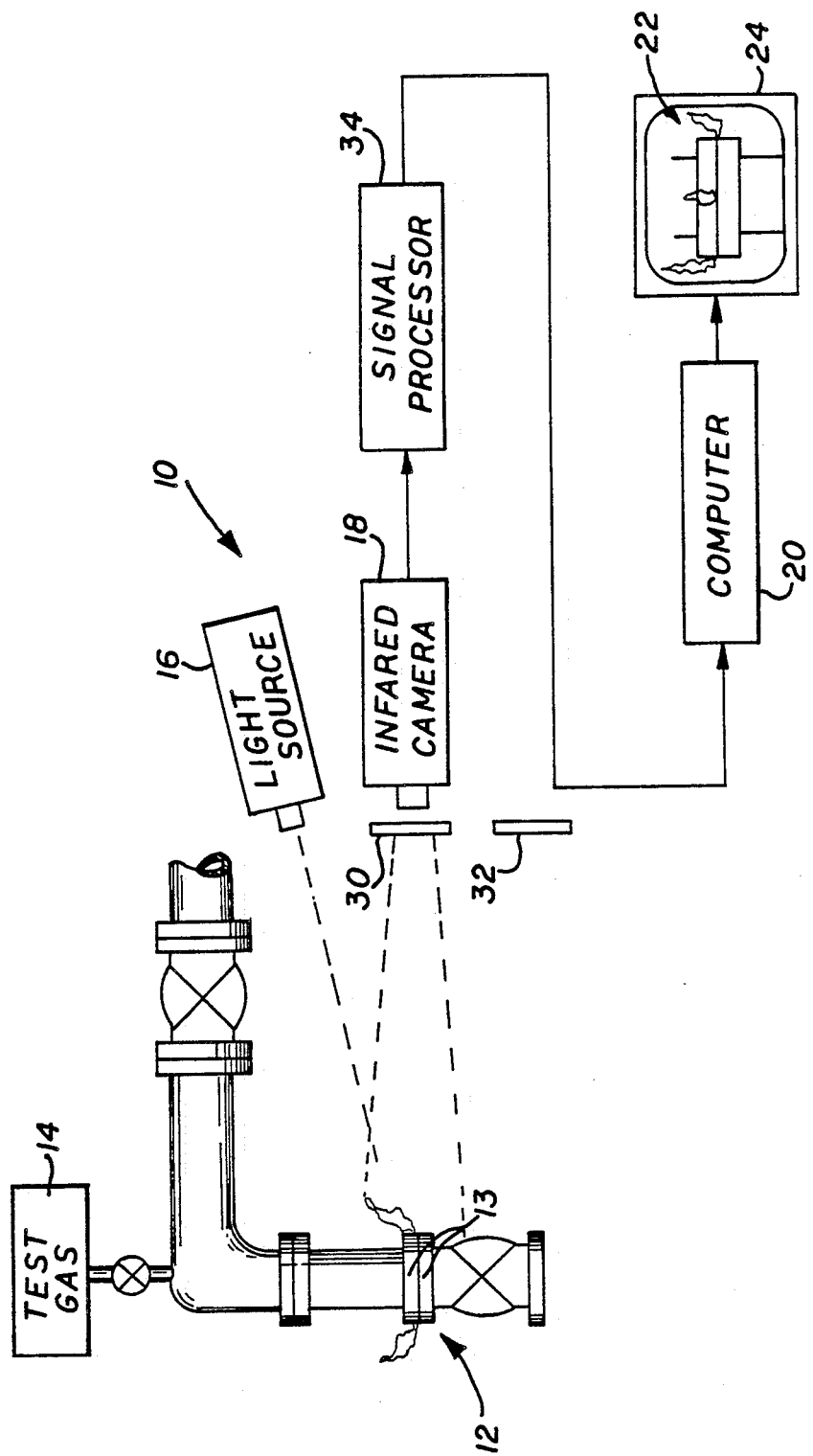
FIG. 1 is a diagrammatic representation of an improved leak detection system embodying the novel features of the invention.

As shown in the exemplary drawings, an improved leak detection system referred to generally in FIG. 1 by the reference numeral 10 is provided for identifying and quantifying leaks in a selected test object 12, such as the illustrative fluid flow conduits. The leak detection system 10 utilizes differential absorption principles in combination with temperature dependent variations in spectral absorption bandwidth of a test gas 14 to permit highly sensitive detection of leaking test gas located substantially at or in close proximity with one or more leak sites. The improved system 10 beneficially compensates for and disregards light absorption attributable to background factors such as trace quantities of the test gas which may be present within an image path.

More particularly, with reference to FIG. 1, the improved leak detection system 10 of the present invention incorporates system components and general operating methods known in the art with respect to differential absorption techniques for locating gas leaks in the test object 12. In this regard, the test object 12 may comprise virtually any structure such as the illustrative flow conduits, rocket engines or components therefor, or any other device for which leak identification and correction is necessary or desirable. In general terms, the test object 12 is charged or pressurized with the test gas 14 chosen for relatively strong light absorptive properties at a particular wavelength, such as sulfur hexafluoride which has high absorptive capabilities in the infrared portion of the spectrum. The pressurized test object 12 is then illuminated by a light source 16 such as a $CO_2$ laser tuned to generate light with a wavelength generally corresponding to or matching the absorptive properties of the test gas. A video camera 18 such as an infrared camera is used to generate an image of the illuminated test object, wherein any leaking test gas disposed along the image path or sight line of the camera will absorb a portion of the light and thus constitute a detectable portion of the generated image. This composite image representing the test gas can be analyzed by a computer 20 on a point-by-point basis for each picture element to yield a visible read-out image 22 on a monitor 24 or the like to identify and quantify leaks. To this point, this differential absorption technique and the related computer analysis are known in the art as described in detail in commonly assigned U.S. Pat. No. 4,772,789, which is incorporated by reference herein.

In accordance with the present invention, the leak detection system 10 is improved by permitting residual or background test gas 14 as well as other background factors to be identified and compensated for to yield a system read-out which essentially focuses only upon test gas located substantially at an actual leakage site or sites on the test object 12. That is, small quantities of the test gas 14 and other air-borne contaminants such as particulate and/or water droplets may be present in the image path of the camera, and may absorb sufficient quantities of the illuminating light to be detectable. Such background factors undesirably reduce the sensitivity or resolution of the system by obscuring the test gas located directly at an actual, on-going leak. In many cases, this background absorption makes it difficult or impossible to pinpoint and quantify an actual leak with the desired accuracy, and/or creates the potential for false readings and false leak alarms. The present invention solves this problem by providing a way to distinguish from the background absorption, and thereby permit background absorption to be disregarded in the final system read-out.

Figure 2:
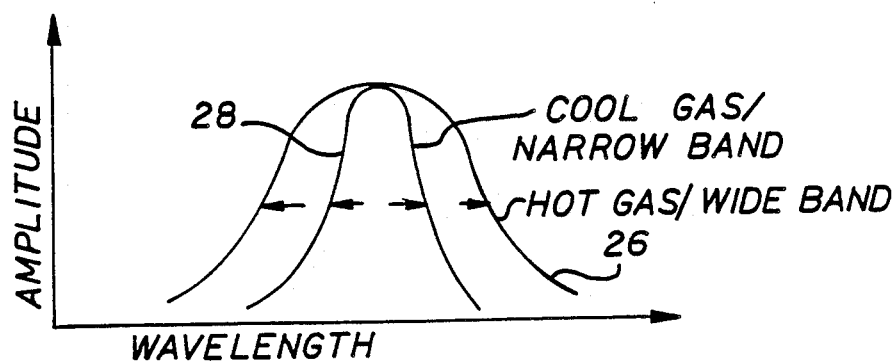
FIG. 2 is a graphic depiction of variation in spectral absorption bandwidth as a function of temperature.

As depicted in FIG. 2, the improved system 10 recognizes that the spectral absorption bandwidth of the test gas 14 varies in accordance with temperature. More specifically, in a heated state, the test gas 14 has a broader bandwidth than in a cooler state, as represented respectively in FIG. 2 by the graphic plots 26 and 28. Therefore, by temperature conditioning the test gas 14 used to pressurize the test object 12, the temperature of test gas leaking from the test object will vary as a general function of distance from the test object. For example, a preheated test gas 14 leaking from the test object will exhibit the heated or relatively high temperature in the immediate vicinity of the test object but will otherwise cool to a lower ambient temperature as the distance from the test object increases. Since the absorptive capacity of the test gas and the illumination characteristics of the light encompass a bandwidth range broader than the specific selected wavelength, this temperature and distance function phenomena can be used in the present invention to compensate for absorption attributable to background factors.

In a preferred form of the invention, the test gas 14 is preheated to a selected elevated temperature relative to the ambient temperature within a test cell facility into which the pressurized test object 12 is placed. The pressurized test object 12 is then illuminated with the specific wavelength source 16, and the camera 18 is used to generate a photographic image of a suspected leak site, such as the interconnected piping flanges 13 shown in FIG. 1. However, the camera 18 is first operated to generate a first image taken through a relatively narrow bandwidth filter 30, such as a filter having a bandwidth corresponding to the light absorption properties of relatively cool test gas as shown by the plot 28 in FIG. 2. This first image is stored in the computer 20 for subsequent process analysis, as will be described.

The camera 18 is then employed to generate a second image of the test object through a relatively broad bandwidth filter 32 (FIG. 1), such as a filter with a bandwidth matching the absorptive properties of the test gas at the elevated temperature as depicted by the plot 26 in FIG. 2. The resultant pair of narrow and broad band images are analyzed by the computer 20, to permit visual display of a leakage read-out analysis on the monitor 24. In this regard, the pair of images in photographic format as taken by the camera 18 are converted on a point-by-point basis for discrete picture elements by a signal processor 34 into the electronic signals for supply to and storage within the computer 20. In a preferred form, the signal processor 34 may comprise a charge coupled device for converting each photographic image to an electronic pulse train which is coupled to a vision board adapted to interpret the pulse train in two-dimensional format for supply to the computer 20. One exemplary charge coupled device for this purpose is marketed by Matsushita Corp., of Japan, under the Model Panasonic GD-CD60. In addition, an exemplary vision board is available from Matrox of Quebec, Canada, under the model designation Imager-At-MVP.

Figure 3:
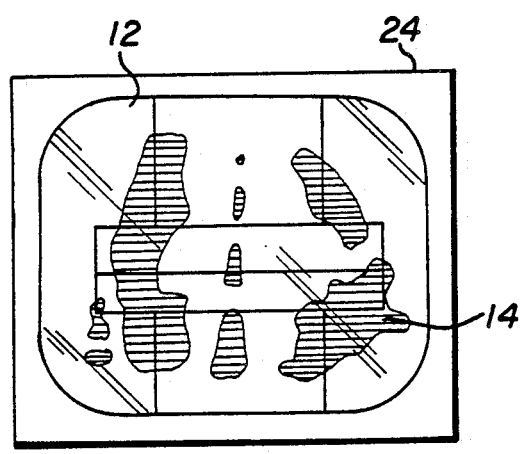
FIG. 3 is a composite image representing a test object and light absorbing gas disposed within an image path.
Figure 4:
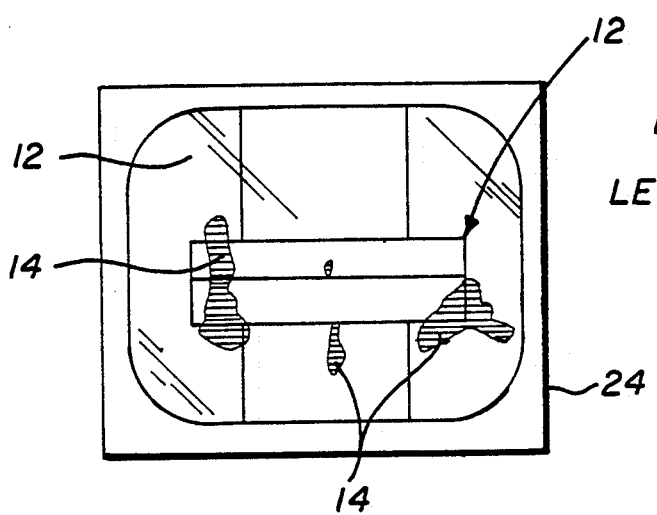
FIG. 4 is an image of the test object similar to FIG. 3, but wherein background factors are eliminated by compensation to identify the light absorbing gas in close proximity with the test object.

The computer 20 analyzes the two images for purposes of background factor compensation in generally the manner described in U.S. Pat. No. 4,772,789 with respect to alternative images. More specifically, as shown in FIG. 3, a composite of both images may be provided as a representation of total light absorption along the image path attributable to leaking gas directly at a leak site as well as that associated with background factors. Importantly, the computer analysis can effectively subtract the effects of the background factors as represented by the narrow band image 28 (FIG. 2) from the absorption due to the higher temperature gas per the broad band image 26, resulting in a highly sensitive and accurate final read-out as depicted in FIG. 4. This final read-out represents only the absorption by heated gas located directly or closely adjacent to an actual leakage site on the test object 12. The undesirable masking of a leak site or leakage magnitude as a result of background absorption by cooler gas is thus avoided.

A variety of modifications and improvements to the improved leak detection system of the present invention will be apparent to those skilled in the art. As one example, while the system has been described with respect to a preheated test gas, it will be understood that a precooled test gas such as a refrigerant or cryogenic may be used and appropriately imaged through the filters 30 and 32 to obtain a specific read-out of low temperature gas at a leak site. Such alternative operation is obtained by appropriate programming of the computer 20 to compensate for warmer background gas located at a distance from the test object, thereby focusing upon colder gas disposed substantially at a leakage site. Moreover, alternative test gases and corresponding light sources of selected wavelength may be used. Accordingly, no limitation on the invention is intended by way of the foregoing description and accompanying drawings, except as set forth in the appended claims.

What is claimed is:

1. A leak detection system for identifying gas leakage from a test object, said system comprising:
    means for charging the test object with a test gas having relatively high absorption characteristics with respect to light of a selected wavelength, said test gas being temperature conditioned to a temperature level significantly different than ambient;
    means for illuminating the charged test object with light having a wavelength corresponding generally with the selected wavelength;
    a pair of filters adapted to permit passage of light corresponding generally with said selected wavelength, said filters having relatively narrow and relatively broad bandwidths, respectively, and thereby defining a narrow band filter and a broad band filter;
    camera means for imaging the charged test object respectively through said narrow band filter and said broad band filter, and for respectively generating a narrow band image and a broad band image; and
    image processor means for comparing said narrow band image and said broad band image to identify gas leakage from the test object.

2. The leak detection system of claim 1 wherein said image processor means includes means for substracting one of said narrow and broad band images from the other.

3. The leak detection system of claim 1 wherein said illuminating means comprises a laser light source tuned to said selected wavelength.

4. The leak detection system of claim wherein the test gas is preheated to a temperature level above ambient.

5. The leak detection system of claim 1 wherein the test gas is precooled to a temperature level below ambient.

6. The leak detection system of claim 1 wherein one of said filters has a bandwidth corresponding generally with the spectral absorption bandwidth of the test gas at ambient temperature, and the other of said filters has a bandwidth corresponding generally with the spectral absorption bandwidth of the test gas at the conditioned temperature level.

7. A leak detection system for identifying gas leakage from a test object, said system comprising:
    means for charging the test object with a test gas having relatively high absorption characteristics with respect to light of a selected wavelength, said test gas being temperature conditioned to a temperature level significantly different than ambient;
    said test gas having a spectral absorption bandwidth which varies as a function of temperature, and wherein test gas leaking from the test object has a temperature level generally corresponding with the conditioned temperature level at a location substantially at the test object, and a temperature level which approaches ambient as a function of increasing distance from the test object;
    means for illuminating the charged test object with light having a wavelength corresponding generally with the selected wavelength;
    a first filter having a spectral bandwidth corresponding generally with the absorption bandwidth of the test gas located substantially at the test object;
    a second filter having a spectral bandwidth corresponding generally with the absorption bandwidth of the test gas at ambient temperature;
    camera means for respectively imaging the charged test object through said first and second filters for respectively generating a pair or images; and
    image processor means for comparing said images to identify gas leakage from the test object.

8. The leak detection system of claim 7 wherein said image processor means include means for subtracting one of said images from the other.

9. The leak detection system of claim 7 wherein said image processor means comprises a computer.

10. A method of identifying gas leakage from a test object, said method comprising the steps of:
    charging the test object with a test gas having relatively high absorption characteristics with respect to light of a selected wavelength, said test gas being temperature conditioned to a temperature level significantly different than ambient;
    illuminating the charged test object with light having a wavelength corresponding generally with the selected wavelength;
    generating a pair of images of the charged test object by imaging the test object respectively through a pair of filters adapted to permit passage of light corresponding generally with the selected wavelength and having relatively narrow and relatively broad bandwidths such that the pair of images respectively define a narrow band image and a broad band image; and
    comparing said narrow band image and said broad band image to identify gas leakage from the test object.

11. The method of claim 10 wherein said comparing step comprises subtracting the images one from the other.

12. The method of claim 10 wherein the charging step includes preheating the test gas to a temperature level above ambient.

13. The method of claim 10 wherein the charging step includes precooling the test gas to a temperature level below ambient.

* * * * *

UNITED STATES PATENT AND TRADEMARK OFFICE
CERTIFICATE OF CORRECTION

PATENT NO. : 5,001,346
DATED : March 19, 1991
INVENTOR(S) : Sarkis Barkhoudarian It is certified that error appears in the above-identified patent and that said Letters Patent is hereby corrected as shown below:

Column 5, Line 64:

after the word claim insert --1--

Signed and Sealed this

Fourth Day of August, 1992

Attest:

DOUGLAS B. COMER

Attesting Officer      Acting Commissioner of Patents and Trademarks